(12) United States Patent
Lensing et al.

(10) Patent No.: US 6,980,300 B1
(45) Date of Patent: Dec. 27, 2005

(54) METHOD AND APPARATUS FOR GENERATING A POLISHING PROCESS ENDPOINT SIGNAL USING SCATTEROMETRY

(75) Inventors: Kevin R. Lensing, Austin, TX (US); James Broc Stirton, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 757 days.

(21) Appl. No.: 09/832,461

(22) Filed: Apr. 11, 2001

(51) Int. Cl.$^7$ ................................. G01B 11/24
(52) U.S. Cl. ................ 356/601; 356/612; 356/446
(58) Field of Search ..................... 356/600, 601, 356/612, 446, 394

(56) References Cited

U.S. PATENT DOCUMENTS

| | | | |
|---|---|---|---|
| 5,393,624 A | | 2/1995 | Ushijima ..................... 430/30 |
| 5,708,506 A | * | 1/1998 | Birang ......................... 356/601 |
| 5,838,447 A | * | 11/1998 | Hiyama et al. ............... 356/600 |
| 5,867,276 A | | 2/1999 | McNeil et al. ............... 356/445 |
| 5,880,838 A | | 3/1999 | Marx et al. .................. 356/351 |
| 6,023,327 A | * | 2/2000 | Shabde et al. ............ 356/237.1 |
| 6,051,348 A | | 4/2000 | Marinaro et al. ............. 430/30 |
| 6,245,584 B1 | | 6/2001 | Marinaro et al. ............. 438/14 |
| 6,291,253 B1 | * | 9/2001 | Lansford et al. .............. 438/14 |
| 6,309,900 B1 | * | 10/2001 | Maury et al. ................. 438/16 |
| 6,433,878 B1 | | 8/2002 | Niu et al. ..................... 356/603 |
| 2002/0135781 A1 | | 9/2002 | Singh et al. ................. 356/601 |

OTHER PUBLICATIONS

Bishop et al., "Use of Scatterometry for resist process control," *SPIE Integrated Circuit Metrology, Inspection and Process Control*, 1673:441–452, 1992.

Hickman et al., "Use of diffracted light from latent images to improve lithography control," *SPIE Integrated Circuit Metrology, Inspection and Process Control*, 1464:245–257, 1991.

McNeil et al., "Scatterometry applied to microelectronics processing—Part 1," *Solid State Technology*, 37(3):29–56, 1993.

(Continued)

*Primary Examiner*—Huy Mai
(74) *Attorney, Agent, or Firm*—Williams, Morgan & Amerson

(57) ABSTRACT

A method for polishing wafers includes polishing a process layer formed on a wafer, the process layer overlying a grating structure; illuminating at least a portion of the process layer and the grating structure; measuring light reflected from the illuminated portion of the process layer and the grating structure to generate a reflection profile; comparing the measured reflection profile to a target reflection profile having an acceptable degree of planarity; and terminating the polishing of the process layer based on the comparison of the measured reflection profile and the target reflection profile. A metrology tool adapted to measure a wafer having a grating structure and a process layer formed over the grating structure after initiation of a polishing process includes a light source, a detector, and a data processing unit. The light source is adapted to illuminate at least a portion of the process layer overlying the grating structure. The detector is adapted to measure light reflected from the illuminated portion of the process layer and the grating structure to generate a reflection profile. The data processing unit is adapted to compare the measured reflection profile to a target reflection profile having an acceptable degree of planarity and generate an endpoint signal based on the comparison of the measured reflection profile and the target reflection profile.

24 Claims, 5 Drawing Sheets

OTHER PUBLICATIONS

Miller and Mellicamp, "Development of an end–point detection procedure for the post–exposure bake process," *Integrated circuit metrology, inspection, and process control IX*: Feb. 20–22, 1995, Santa Clara, California, *SPIE Integrated Circuit Metrology, Inspection and Process Control*, 2439:78–88, 1995.

Milner et al., "Latent image exposure monitor using scatterometry," *SPIE Integrated Circuit Metrology, Inspection and Process Control*, 1673:274–283, 1992.

Prins et al., "Scatterometric sensor for PEB process control," *Metrology, inspection, and process control for microlithogtaphy, X*:Mar. 11–13, 1996, Santa Clara, California , *SPIE Intregated Circuit Metrology, Inspection and Process Control*,2725:710–719, 1996.

Raymond et al., "Multiparameter process metrology using scatterometry," In: *Optical characterization techniques for high–performance microelectronic device manufacturing II, SPIE—The International Society for Optical Engineering*, 2638:84–93, Austin, Texas, Oct. 25–26, 1995.

Raymond et al., "Scatterometric sensor for lithography," In: *Manufacturing process control for microelectronic devices and circuits, SPIE—The International Society for Optical Engineering*, 2336:37–49, Austin, Texas, Oct. 20–21, 1994.

Sturtevant et al., "Post–exposure bake as a process–control parameter for chemically–amplified photoresist," *Metrology, inspection, and process control for microlithogtaphy, VII:* Mar. 2–4, 1993, Santa Jose, California, *SPIE Integrated Circuit Metrology, Inspection and Process Control*, vol. 1926, 1993.

Sturtevant et al., "Use of scatterometric latent image detector in closed loop feedback control of linewidth," *SPIE Integrated Circuit Metrology, Inspection and Process Control*, 2196:352–359, 1994.

* cited by examiner

METHOD AND APPARATUS FOR GENERATING A POLISHING PROCESS ENDPOINT SIGNAL USING SCATTEROMETRY

BACKGROUND OF THE INVENTION

1. Field of the Invention

This invention relates generally to the field of semiconductor device manufacturing and, more particularly, to a method and apparatus for generating a polishing process endpoint signal using scatterometry.

2. Description of the Related Art

Chemical mechanical polishing (CMP) is a widely used means of planarizing silicon dioxide as well as other types of layers on semiconductor wafers. Chemical mechanical polishing typically utilizes an abrasive slurry disbursed in an alkaline or acidic solution to planarize the surface of the wafer through a combination of mechanical and chemical action. Generally, a chemical mechanical polishing tool includes a polishing device positioned above a rotatable circular platen or table on which a polishing pad is mounted. The polishing device may include one or more rotating carrier heads to which wafers may be secured, typically through the use of vacuum pressure. In use, the platen may be rotated and an abrasive slurry may be disbursed onto the polishing pad. Once the slurry has been applied to the polishing pad, a downward force may be applied to each rotating carrier head to press the attached wafer against the polishing pad. As the wafer is pressed against the polishing pad, the surface of the wafer is mechanically and chemically polished.

As semiconductor devices are scaled down, the importance of chemical mechanical polishing to the fabrication process increases. In particular, it becomes increasingly important to control and minimize within-wafer topography variations. For example, in one embodiment, to minimize spatial variations in downstream photolithography and etch processes, it is necessary for the thicknesses of the process layer (e.g., silicon dioxide) formed an a wafer to be as uniform as possible (i.e., it is desirable for the surface of the process layer to be as planar as possible).

Those skilled in the art will appreciate that a variety of factors may contribute to producing variations across the post-polish surface of a process layer. For example, variations in the surface of the wafer may be attributed to drift of the chemical mechanical polishing device. Typically, a chemical mechanical polishing device is optimized for a particular process, but because of chemical and mechanical changes to the polishing pad during polishing, degradation of process consumables, and other processing factors, the chemical mechanical polishing process may drift from its optimized state.

Typically, the operating recipes for polishing tools are determined during the process characterization stage, because no in-line techniques are readily available for determining the planarity of the polished surface. Based on design factors, such as the topology of the underlying features and the thickness of the layer to be polished, polishing targets are generated to help ensure that the polishing time is sufficient to planarize the process layer being polished without overpolishing and damaging the underlying structures. FIG. 1A illustrates a cross-section of an exemplary semiconductor device 100 that is subjected to a planarization process. The semiconductor device 100 includes a plurality of interconnect structures 110 (e.g., aluminum stacks) formed on a previous interlayer dielectric (ILD) layer 120 (e.g., silicon dioxide formed using tetraethoxysilane (TEOS) or fluorine doped tetraethoxysilane (F-TEOS)). For clarity and ease of illustration, not all features of the interconnect structures 110 are shown. Typically, an aluminum interconnect stack includes a titanium layer over the ILD layer 120, a titanium nitride layer, an aluminum layer, a second titanium nitride layer, and a silicon oxide hard mask layer. A second ILD layer 130 is formed over the interconnect structures 110. The ILD layer 130 is polished to produce an approximately planar surface 135 of the ILD layer 130, as shown in FIG. 1B. If the ILD layer 130 is underpolished, the surface 135 will not be as planar as desired, which may interfere with formation of features in subsequent layers. If the ILD layer 130 is overpolished, the insulative capability of the ILD layer 130 may be reduced.

Other exemplary process layers that are commonly subjected to polishing processes are ILD layers formed over transistor gate electrode stacks or silicon dioxide layers used to form shallow trench isolation (STI) structures formed in a substrate between active devices (e.g., transistors) in the semiconductor device. Overpolishing or underpolishing may also cause problems with these structures.

The present invention is directed to overcoming, or at least reducing the effects of, one or more of the problems set forth above.

SUMMARY OF THE INVENTION

One aspect of the present invention is seen in a method for polishing wafers. The method includes polishing a process layer formed on a wafer, the process layer overlying a grating structure; illuminating at least a portion of the process layer and the grating structure; measuring light reflected from the illuminated portion of the process layer and the grating structure to generate a reflection profile; comparing the measured reflection profile to a target reflection profile having an acceptable degree of planarity; and terminating the polishing of the process layer based on the comparison of the measured reflection profile and the target reflection profile.

Another aspect of the present invention is seen in a metrology tool adapted to measure a wafer having a grating structure and a process layer formed over the grating structure after initiation of a polishing process. The metrology tool includes a light source, a detector, and a data processing unit. The light source is adapted to illuminate at least a portion of the process layer overlying the grating structure. The detector is adapted to measure light reflected from the illuminated portion of the process layer and the grating structure to generate a reflection profile. The data processing unit is adapted to compare the measured reflection profile to a target reflection profile having an acceptable degree of planarity and generate an endpoint signal based on the comparison of the measured reflection profile and the target reflection profile.

BRIEF DESCRIPTION OF THE DRAWINGS

The invention may be understood by reference to the following description taken in conjunction with the accompanying drawings, in which like reference numerals identify like elements, and in which.

Figure 1A:
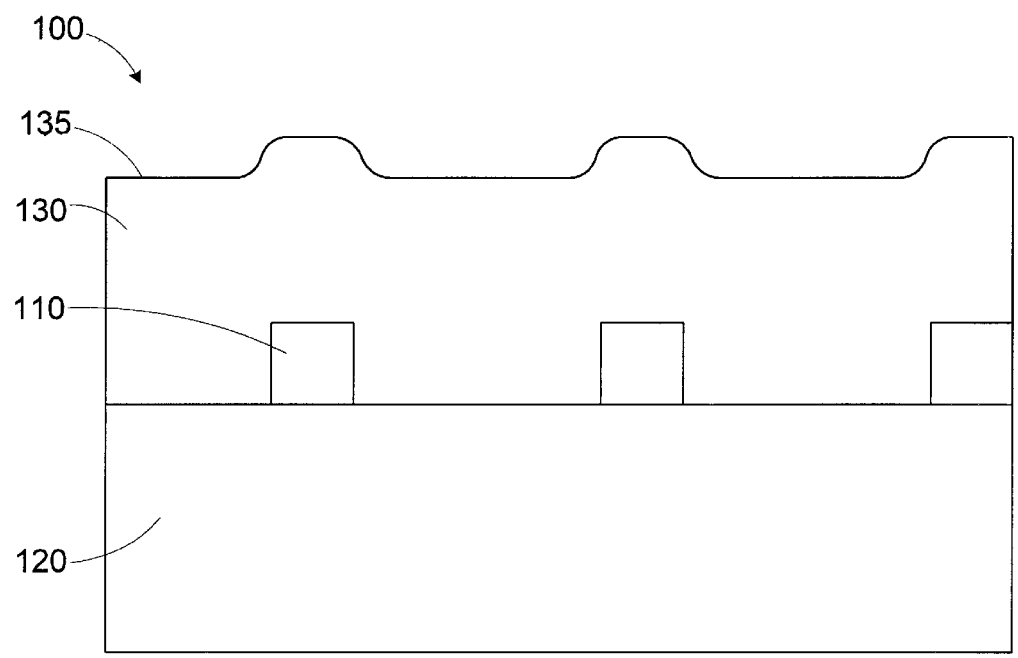
FIGS. 1A and 1B are cross sections of an exemplary semiconductor device on which a polishing process is performed.
Figure 1B:
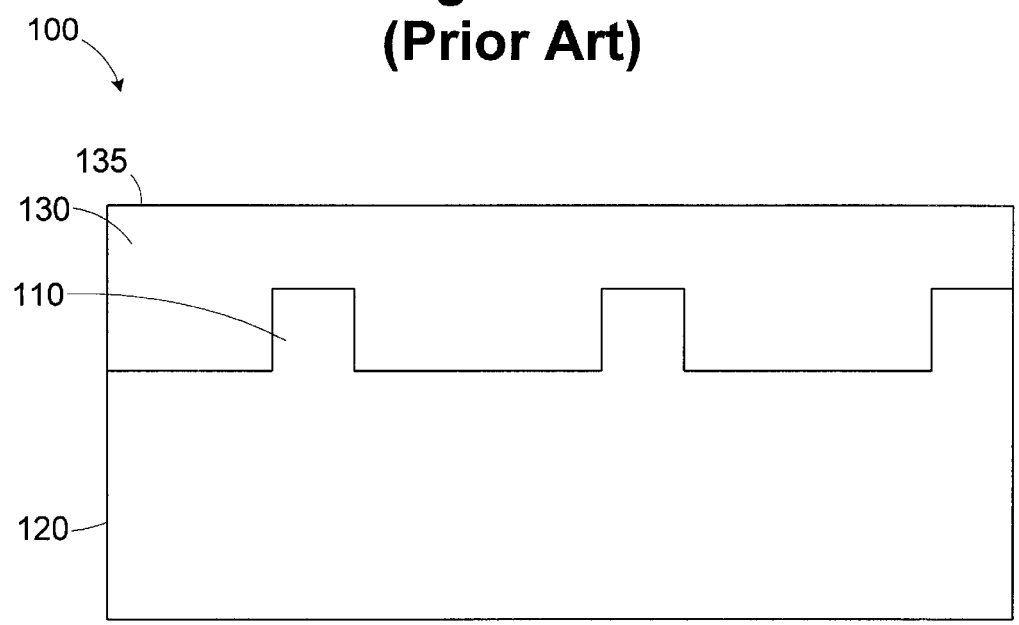

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
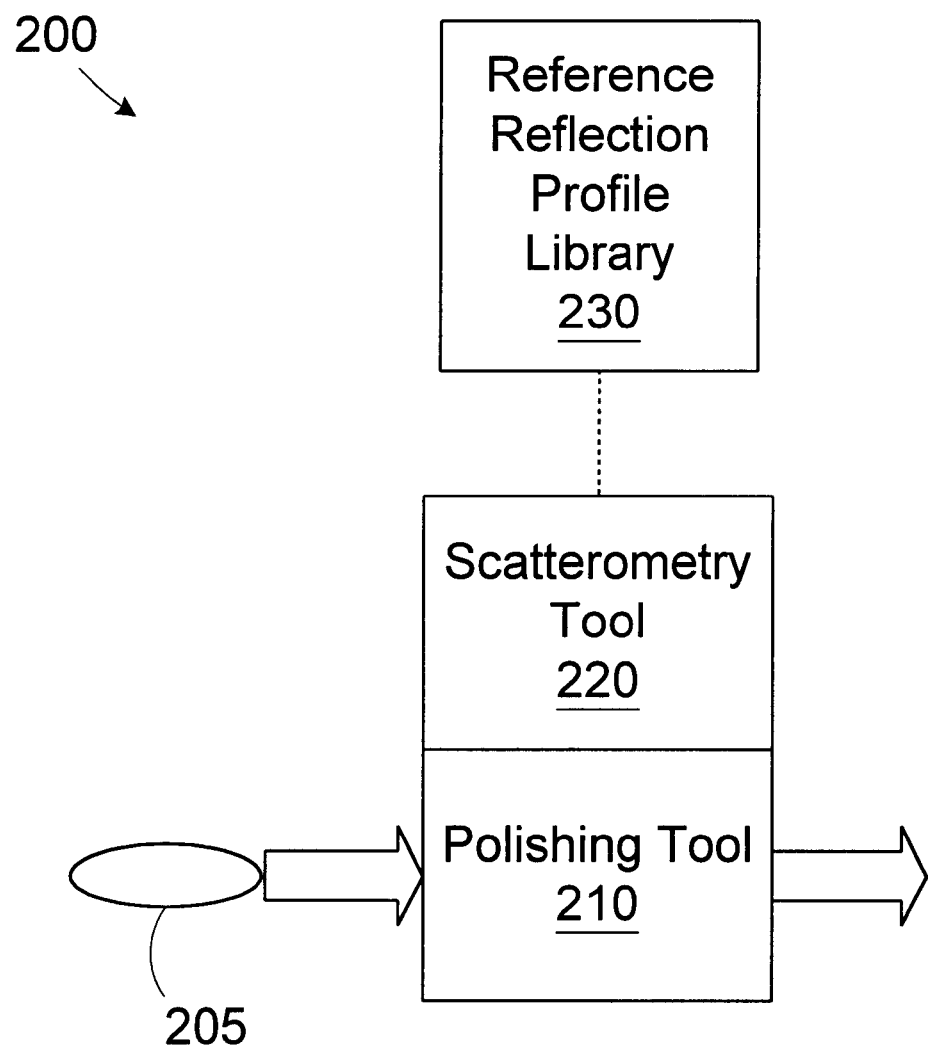
FIG. 2 is a simplified diagram of an illustrative processing line for processing wafers in accordance with one illustrative embodiment of the present invention.

Referring to FIG. 2, a simplified diagram of an illustrative processing line 200 for processing wafers 205 in accordance with one illustrative embodiment of the present invention is provided. The processing line 200 includes a polishing tool 210 for polishing the wafers 205 in accordance with a polishing recipe. The polishing tool 210 may be used to polish process layers formed on the wafer 205, such as the ILD layers described above, metal layers, or other process layers.

The polishing tool 210 has an associated in-situ a scatterometry tool 220 adapted to measure the planarity of the polished process layer on the wafer after the polishing process has started. The polishing process may be temporarily suspended to allow the scatterometry tool 220 to measure the planarity, or the scatterometry tool 220 may be adapted to perform sample measurements at specific intervals to ensure exposure to the grating structure without pausing the polishing process. In general, the scatterometry tool 220 includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by Thermawave, Inc. of Freemont Calif. The data processing unit may comprise a profile application server manufactured by Timbre Technologies, a fully owned subsidiary of Tokyo Electron America, Inc. of Austin, Tex. and distributed by Thermawave, Inc.

The scatterometry tool 220 provides an endpoint signal for terminating the polishing process in the polishing tool 210. That is, after the polishing process is started, the scatterometry tool 220 is used to obtain an optical reflection profile of the process slayer being polished at various times. The frequency of the measurements taken by the scatterometry tool 220 may be varied as a matter of design choice. For example, during a typical polishing process, the scatterometry tool 220 may generate a reflection profile approximately every 1–3 seconds. Measurements may also be taken at different rates during the duration of the polishing process, i.e., more measurements may be taken as the process nears endpoint. The polishing process may or may not be stopped during the period when the scatterometry measurements are being taken.

In one embodiment, the scatterometry tool 220 measures the planarity of a process layer formed in production devices. In some cases, the geometry of the features or the presence of underlying structures may inhibit scatterometry measurements. Accordingly, test structures having the same general configuration as features of the production devices formed on the wafer 205 may be employed. The test structures may be formed in a region of the wafer 205 not normally used for forming devices (e.g., in the periphery region where identification codes are typically scribed or in the scribe lines between production die).

Figure 3:
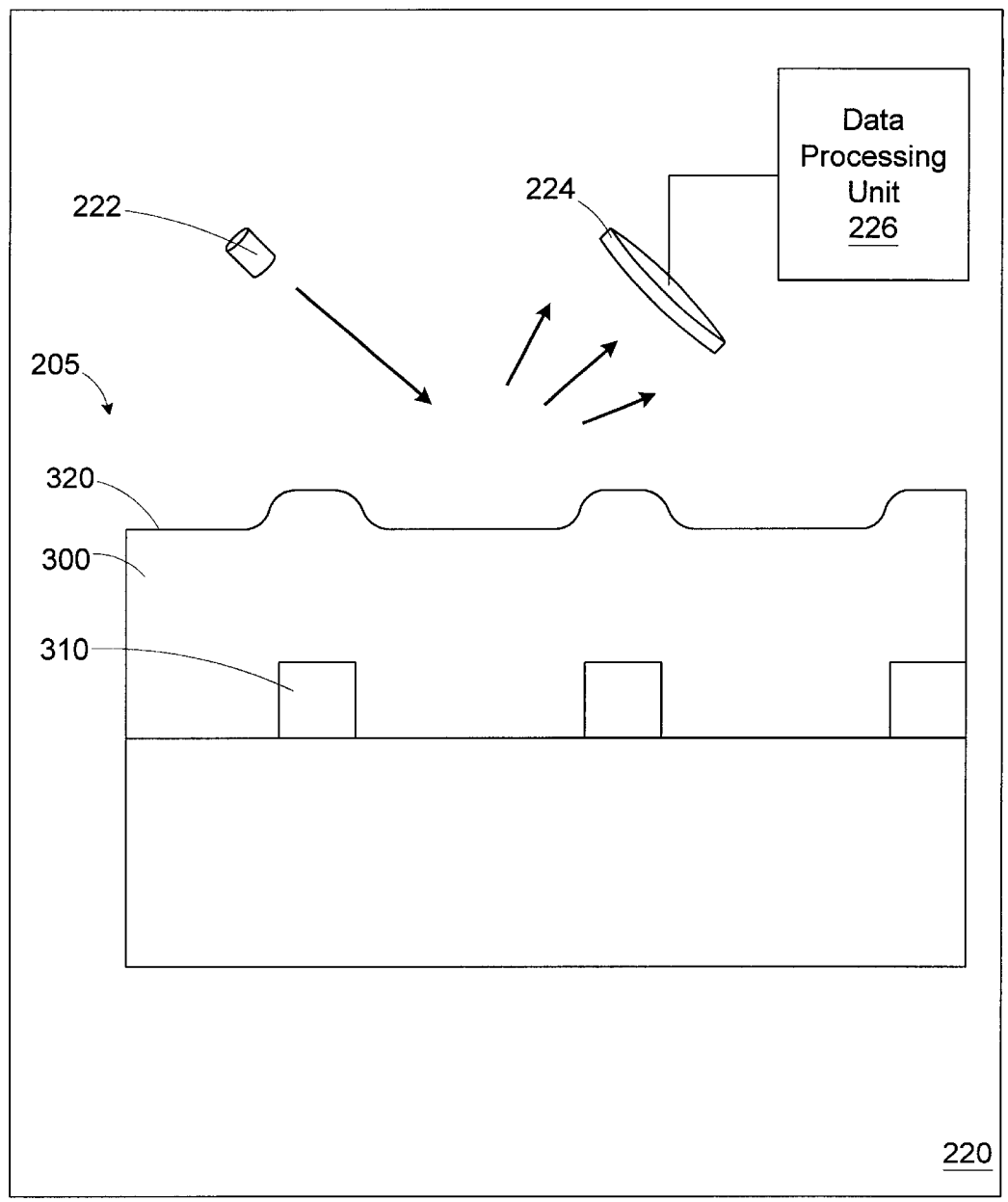
FIG. 3 is a simplified view of the scatterometry tool of FIG. 3 loaded with a wafer.

Turning now to FIG. 3, a simplified view of the scatterometry tool 220 loaded with a wafer 205 having a process layer 300 is provided. In the illustrated embodiment, the process layer 300 is formed over a grating structure 310, such as interconnect structures or a test structure). The scatterometry tool 220, includes a light source 222 and a detector 224 positioned proximate the process layer 300. The light source 222 of the scatterometry tool 220 illuminates at least a portion of the process layer 300 and the grating structure 310, and the detector 224 takes optical measurements, such as intensity or phase, of the reflected light. A data processing unit 226 receives the optical measurements from the detector 224 and processes the data to determine the planarity of the surface 320 of the process layer 300.

The scatterometry tool 220 may use monochromatic light, white light, or some other wavelength or combinations of wavelengths, depending on the specific implementation. The angle of incidence of the light may also vary, depending on the specific implementation. The light analyzed by the scatterometry tool 220 typically includes a reflected component (i.e., incident angle equals reflected angle) and a refracted component (i.e., incident angle does not equal the reflected angle). For purposes of discussion here, the term "reflected" light is meant to encompass both components.

Variations in the process layer 300 caused by differing degrees of planarity causes changes in the reflection profile (e.g., intensity vs. wavelength–tan($\delta$), phase vs. wavelength–sin($\psi$), where $\delta$ and $\psi$ y are common scatterometry outputs known to those of ordinary skill in the art) measured by the scatterometry tool 220 as compared to the light scattering profile that would be present in a wafer having a process layer 300 with an approximately planar surface.

Figure 4A:
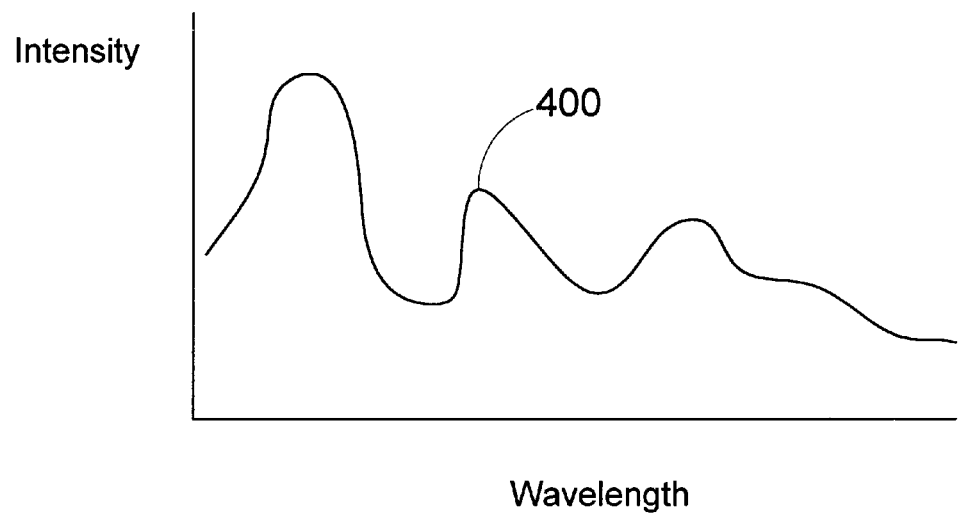
FIG. 4A illustrates a target scatterometry profile used by the scatterometry tool of FIG. 3 to determine an endpoint for the polishing process performed by the polishing tool of FIG. 2.

FIG. 4A illustrates an exemplary target reflection profile 400 that may be included in a reference reflection profile library 232 (see FIG. 2) used by the data processing unit 226 to characterize the planarity of the process layer 300 as compared to the measured reflection profile of the process layer 300. The target reflection profile 400 represents a calculated or measured reflection profile for a process layer 300 having an ideal or acceptable planarization profile. The particular reflection profile expected for any structure depends on the specific geometry of the structure and the parameters of the measurement technique employed by the scatterometry tool 220 (e.g., light bandwidth, angle of incidence, etc.). The target reflection profile 400 may be calculated using Maxwell's equations based on the characteristics of the process layer 300 and underlying topology of the grating structure 310. Reference scatterometry libraries are commercially available from Timbre Technologies, Inc. The target reflection profile 400 may also be generated empirically by measuring the reflection profiles of a sample "known good" wafer characterized by destructive or non-destructive examination techniques.

Figure 4B:
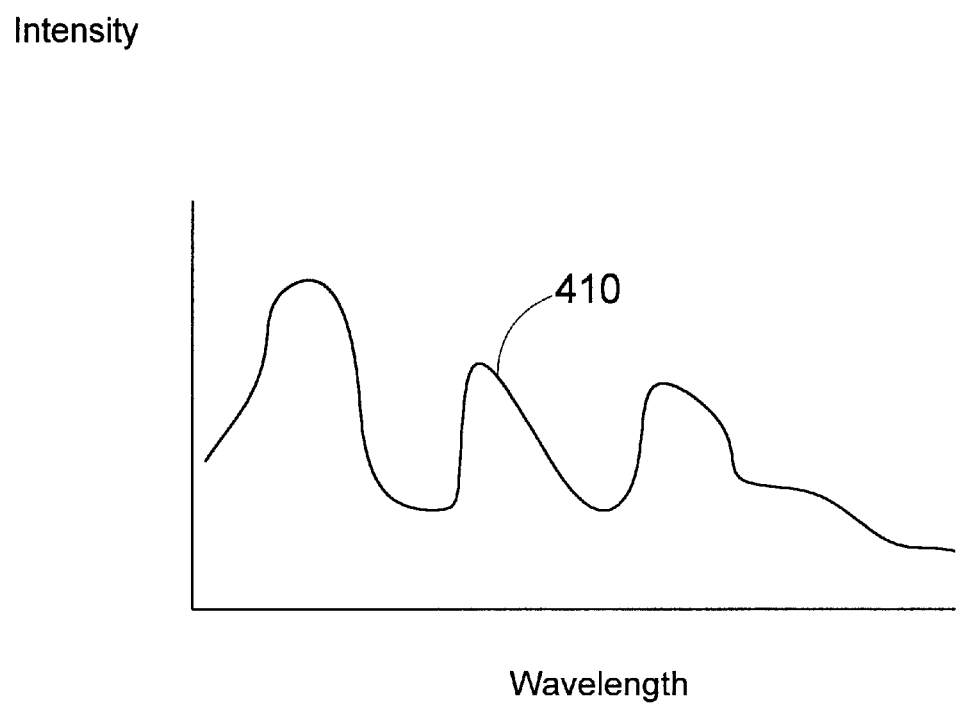
FIG. 4B illustrates a measured scatterometry profile generated by the scatterometry tool of FIG. 3 for comparison to the target scatterometry profile of FIG. 4A.

FIG. 4B represents a measured reflection profile 410 generated by the scatterometry tool 200 at some time after the polishing of a wafer including the process layer 300 and grating structure 310 is started. The data processing unit 226 compares the measured reflection profile 410 to the target reflection profile 400 to determine when an acceptable level of planarity exists on the process layer 300. The measured reflection profile 410 represents a process layer 300 having an unknown degree of planarity. The scatterometry tool 220 periodically generates the measured reflection profile 410 and compares it to the target reflection profile 400. Particular techniques for determining the "fit" between the target reflection profile 400 and the measured reflection profile 410 are well known to those of ordinary skill in the art. One exemplary technique includes determining the mean squared distance between the target reflection profile 400 and the measured reflection profile 410.

When the difference between the target reflection profile 400 and the measured reflection profile 410 is less than a predetermined threshold, the scatterometry tool 220 sends an endpoint signal to the polishing tool 210 to terminate the polishing process. The specific threshold employed depends on the comparison technique used and the accuracy of the scatterometric measurements.

Figure 5:
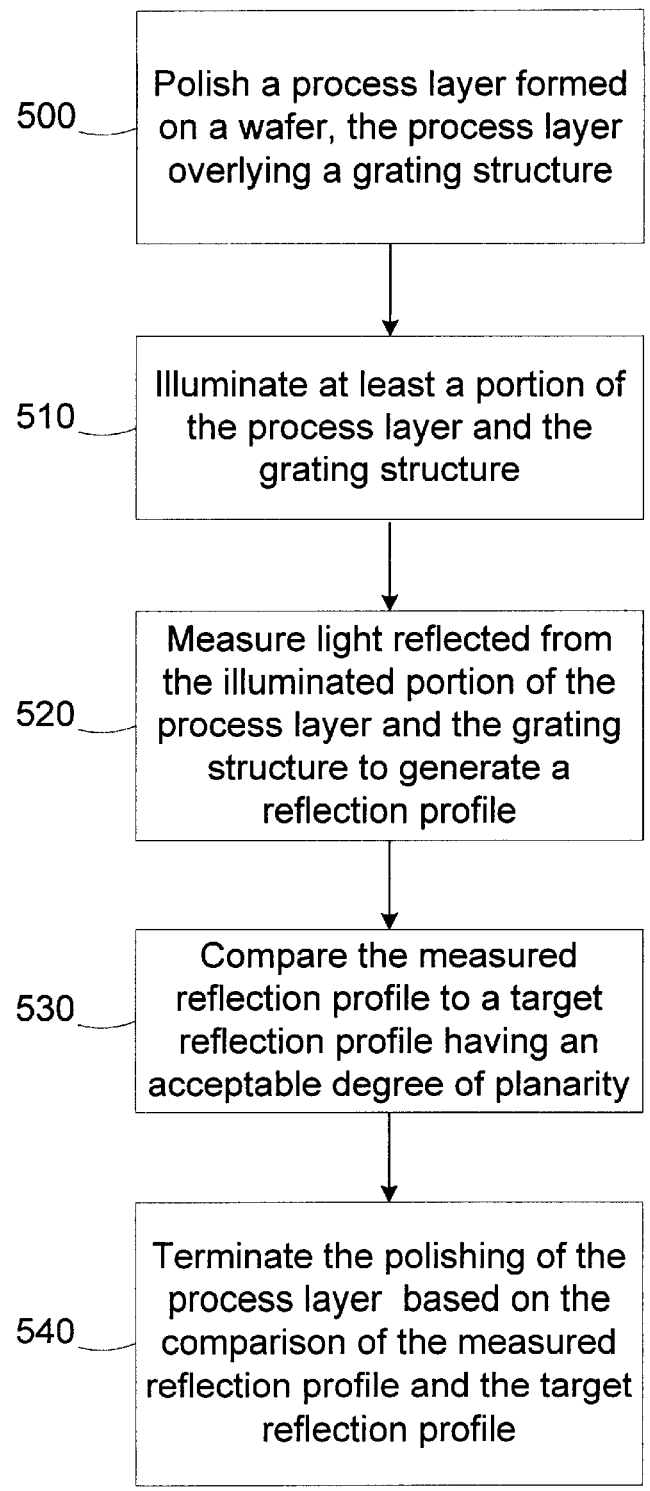
FIG. 5 is a simplified flow diagram of a method for controlling a polishing process in accordance with another illustrative embodiment of the present invention.

FIG. 5 is a simplified flow diagram of a method for controlling a polishing process in accordance with an illustrative embodiment of the present invention. In block 500, a process layer formed on a wafer overlying a grating structure is polished. In block 510, at least a portion of the process layer and the grating structure is illuminated. In block 520, light reflected from the illuminated portion of the process layer and the grating structure is measured to generate a reflection profile. In block 530, the measured reflection profile is compared to a target reflection profile having an acceptable degree of planarity. In block 540, the polishing of the process layer is terminated based on the comparison of the measured reflection profile and the target reflection profile.

Controlling the polishing tool 210 based on feedback from the scatterometry tool 220, as described above, has numerous advantages. The uniformity of the polishing operation may be increased. Decreased planarization variation reduces the likelihood that a wafer requires rework or must be scrapped. Accordingly, the quality of the devices produced on the processing line 200 and the efficiency of the processing line 200 are both increased. Manufacturing efficiency is also greatly increased. Currently, there is no non-destructive in-line method for determining wafer planarity, so the thin film deposition and subsequent CMP operations contain a great deal of process latitude that translate as unnecessary uses of consumables and processing time. A planarity-based endpoint system allows the elimination of such unnecessary deposition and polishing.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for determining planarity, comprising:
   polishing a process layer formed on a wafer, the process layer overlying a grating structure;
   illuminating at least a portion of the process layer and the grating structure;
   measuring light reflected from the illuminated portion of the process layer and the grating structure to generate a reflection profile;
   comparing the measured reflection profile to a target reflection profile having an acceptable degree of planarity; and
   terminating the polishing of the process layer based on the comparison of the measured reflection profile and the target reflection profile.

2. The method of claim 1, wherein terminating the polishing further comprises terminating the polishing of the process layer in response to the difference between the measured reflection profile and the target reflection profile being less than a predetermined threshold.

3. The method of claim 2, wherein comparing the measured reflection profile to the target reflection profile further comprises determining a mean squared distance between the measured reflection profile and the target reflection profile.

4. The method of claim 3, wherein terminating the polishing of the process layer further comprises terminating the polishing of the process layer in response to the mean squared distance between the measured reflection profile and the target reflection profile being less than the predetermined threshold.

5. The method of claim 1, wherein generating the reflection profile comprises generating the reflection profile based on at least one of intensity and phase of the reflected light.

6. The method of claim 1, wherein providing the wafer comprises providing the wafer having the grating structure formed in a test structure on the wafer.

7. The method of claim 1, wherein providing the wafer comprises providing the wafer with the grating structure formed in a production device on the wafer.

8. A metrology tool adapted to measure a wafer having a grating structure and a process layer formed over the grating structure after initiation of a polishing process, comprising:
   a light source adapted to illuminate at least a portion of the process layer overlying the grating structure;
   a detector adapted to measure light reflected from the illuminated portion of the process layer and the grating structure to generate a reflection profile; and
   a data processing unit adapted to compare the measured reflection profile to a target reflection profile having an acceptable degree of planarity and generate an endpoint signal based on the comparison of the measured reflection profile and the target reflection profile.

9. The metrology tool of claim 8, wherein the data processing unit is further adapted to terminate the polishing of the process layer in response to the difference between the measured reflection profile and the target reflection profile being less than a predetermined threshold.

10. The metrology tool of claim 9, wherein the data processing unit is further adapted to determine a mean squared distance between the measured reflection profile and the target reflection profile.

11. The metrology tool of claim 10, wherein the data processing unit is further adapted to generate the endpoint signal in response to the mean squared distance between the measured reflection profile and the target reflection profile being less than the predetermined threshold.

12. The metrology tool of claim 8, wherein the detector is further adapted to generate the reflection profile based on at least one of intensity and phase of the reflected light.

13. The metrology tool of claim 8, wherein the metrology tool comprises at least one of a scatterometer, an ellipsometer, and a reflectometer.

14. The metro logy tool of claim 8, wherein the grating structure comprises a test structure.

15. The metrology tool of claim 8, wherein the grating structure comprises a portion of a production device formed on the wafer.

16. A processing line, comprising:
   a polishing tool adapted to polish a process layer formed on a wafer, the process layer overlying a grating structure; and
   a metrology tool comprising:
      a light source adapted to illuminate at least a portion of the process layer overlying the grating structure;
      a detector adapted to measure light reflected from the illuminated portion of the process layer and the grating structure to generate a reflection profile; and
      a data processing unit adapted to compare the measured reflection profile to a target reflection profile having an acceptable degree of planarity and generate an endpoint signal based on the comparison of the measured reflection profile and the target reflection profile.

17. The metrology tool of claim 16, wherein the data processing unit is further adapted to terminate the polishing of the process layer in response to the difference between the measured reflection profile and the target reflection profile being less than a predetermined threshold.

18. The processing line of claim 17, wherein the data processing unit is further adapted to determine a mean squared distance between the measured reflection profile and the target reflection profile.

19. The processing line of claim 18, wherein the data processing unit is further adapted to generate the endpoint signal in response to the mean squared distance between the measured reflection profile and the target reflection profile being less than the predetermined threshold.

20. The processing line of claim 16, wherein the detector is further adapted to generate the reflection profile based on at least one of intensity and phase of the reflected light.

21. The processing line of claim 16, wherein the metrology tool comprises at least one of a scatterometer, an ellipsometer, and a reflectometer.

22. The processing line of claim 16, wherein the grating structure comprises a test structure.

23. The processing line of claim 16, wherein the grating structure comprises a portion of a production device formed on the wafer.

24. A processing line, comprising:
   means for polishing a process layer formed on a wafer, the process layer overlying a grating structure;
   means for illuminating at least a portion of the process layer and the grating structure;
   means for measuring light reflected from the illuminated portion of the process layer and the grating structure to generate a reflection profile;
   means for comparing the measured reflection profile to a target reflection profile having an acceptable degree of planarity; and
   means for terminating the polishing of the process layer based on the comparison of the measured reflection profile and the target reflection profile.

* * * * *

UNITED STATES PATENT AND TRADEMARK OFFICE
CERTIFICATE OF CORRECTION

PATENT NO. : 6,980,300 B1  Page 1 of 1
DATED : December 27, 2005
INVENTOR(S) : Kevin R. Lensing and James Broc Stirton It is certified that error appears in the above-identified patent and that said Letters Patent is hereby corrected as shown below:

<u>Column 7,</u>
Line 18, delete "metro logy," and insert -- metrology --.

Signed and Sealed this

Eleventh Day of April, 2006

JON W. DUDAS
*Director of the United States Patent and Trademark Office*